(12) United States Patent
Kirkwood (10) Patent No.: US 7,334,275 B1
(45) Date of Patent: Feb. 26, 2008

(54) MOBILITY ASSISTANCE DEVICE

(76) Inventor: Susan Kirkwood, 2600 Lincolnway Farms Rd., Wooster, OH (US) 44691

( * ) Notice: Subject to any disclaimer, the term of this patent is extended or adjusted under 35 U.S.C. 154(b) by 26 days.

(21) Appl. No.: 10/711,597

(22) Filed: Sep. 28, 2004

(51) Int. Cl.
*A61G 7/10* (2006.01)
*A61F 5/37* (2006.01)

(52) U.S. Cl. ............... 5/81.1 R; 5/81.1 T; 128/876; 128/882; D24/190

(58) Field of Classification Search ............... 5/81.1 R, 5/83.1, 89.1, 81.1 T; 128/869, 876, 878, 128/879, 881, 882; 602/19–21, 23–29; D24/190, D24/192
See application file for complete search history.

(56) References Cited

U.S. PATENT DOCUMENTS

| 3,598,114 | A | * | 8/1971 | Lewis | 602/19 |
| 4,392,489 | A | * | 7/1983 | Wagner, Sr. | 602/24 |
| 4,461,288 | A | * | 7/1984 | Curtis | 602/23 |
| 4,598,701 | A | * | 7/1986 | Schaefer | 602/19 |
| 4,609,188 | A | * | 9/1986 | Lind | 482/140 |
| 4,649,939 | A | * | 3/1987 | Curtis | 602/27 |
| 4,679,263 | A | * | 7/1987 | Honer | 5/640 |
| 4,736,477 | A | * | 4/1988 | Moore | 5/648 |
| D296,930 | S | * | 7/1988 | Carabelli | D24/190 |
| 4,805,605 | A | * | 2/1989 | Glassman | 602/24 |
| 4,910,831 | A | * | 3/1990 | Bingold | 24/16 PB |
| 4,942,644 | A | * | 7/1990 | Rowley | 24/16 PB |
| 5,076,288 | A | * | 12/1991 | Millard et al. | 128/869 |
| 5,159,728 | A | * | 11/1992 | Bingold | 24/16 PB |
| 5,165,122 | A | * | 11/1992 | Phalen | 5/81.1 T |
| D332,663 | S | * | 1/1993 | Liszewski | D24/190 |
| 5,179,942 | A | * | 1/1993 | Drulias et al. | 128/101.1 |
| 5,205,814 | A | * | 4/1993 | Lundrigan et al. | 602/19 |
| 5,211,186 | A | * | 5/1993 | Shoemaker et al. | 5/628 |
| D347,156 | S | * | 5/1994 | Starrett et al. | D29/120.2 |
| 5,398,383 | A | * | 3/1995 | Bingold | 24/16 PB |
| D373,826 | S | * | 9/1996 | Pujals, Jr. | D24/190 |
| 5,708,998 | A | * | 1/1998 | Torbik | 5/636 |
| 5,802,888 | A | * | 9/1998 | Parsons | 70/16 |
| 5,963,995 | A | * | 10/1999 | Glass | 5/81.1 R |
| 6,364,257 | B1 | * | 4/2002 | Holder | 248/74.3 |
| 6,859,965 | B1 | * | 3/2005 | Gourd | 5/646 |
| 7,160,262 | B2 | * | 1/2007 | Wicks | 602/19 |
| 2006/0185078 | A1 | * | 8/2006 | Perry | 5/81.1 T |
| 2006/0272367 | A1 | * | 12/2006 | Kriesel | 70/16 |

OTHER PUBLICATIONS

Gershman, Maurice, M.D. "Self-Adhering Nylon Tapes." Journal of A.M.A. (vol. 168, No. 7) Oct. 18, 1958.*

* cited by examiner

*Primary Examiner*—Robert G. Santos
(74) *Attorney, Agent, or Firm*—Nancy Lynn Reeves; Walker & Jocke (57) ABSTRACT

A mobility assistance device to assist a caregiver to lift and move the legs of a patient with limited mobility while maintaining the relative position of each leg with respect to the other. The mobility assistance device wraps around and stabilizes the patient's legs and provides a single hand grip that may be used to lift and rotate the patient's legs in unison.

23 Claims, 8 Drawing Sheets

Figure 9

MOBILITY ASSISTANCE DEVICE

TECHNICAL FIELD

This invention relates generally to mobility aids. Specifically, this invention relates to an apparatus to assist a caregiver in moving the legs of a patient following hip surgery.

BACKGROUND ART

Individuals who have hip replacement surgery must occasionally move about during the early healing stages following surgery. During this period, both legs must be moved in unison without twisting, and particularly without permitting the ankles to cross. If the legs are not moved in unison, or the ankles cross, the pain can be excruciating.

Currently, a caregiver accomplishes this by grasping the legs or ankles of the patient who has had surgery and gently swinging him or her around to a sitting position, or other desired position, paying particular attention to maintain the relative position of each leg with respect to the other. Another method of moving a patient's legs involves the caregiver placing his or her forearm under the legs of the patient needing assistance and the caregiver stabilizing the patient's legs on the forearm of the caregiver using the other arm. It is very difficult for the caregiver to move both legs in unison using either of the above methods and, as noted above, the failure to do so can be quite painful. Coordinated movement of the legs of another individual is especially difficult when the caregiver is small relative to the size of the patient needing assistance. In addition, the posture the caregiver is required to maintain, particularly using the second method of providing assistance, can cause back strain in the caregiver.

In addition to post hip replacement patients, who might suffer extreme pain because of such assistance if not provided with extreme care, a variety of other individuals may also need assistance in moving their legs. These individuals may include elderly individuals and individuals with paraplegia, quadriplegia, post-polio syndrome, multiple sclerosis, or any other ailment that temporarily or permanently hinders independent mobility.

Thus, there is a need for an apparatus that can be used to assist a caregiver in moving an individual's legs from one position to another in a manner that does not cause additional pain or increase the risk of injury for either the caregiver or the patient. This apparatus is particularly needed for use following hip replacement surgery.

DISCLOSURE OF INVENTION

It is an object of an exemplary form of the present invention to provide an apparatus that can be used to move the legs of an individual who is unable to easily move them without assistance.

It is a further object of an exemplary form of the present invention to provide an apparatus that can be used to assist a first individual in moving the legs of a second individual while maintaining the position of each of the second individual's legs relative to the other.

It is a further object of an exemplary form of the present invention to provide an apparatus that can be used by a first individual to move the legs of a second individual with one hand while maintaining the position of the second individual's each leg relative to the other.

It is a further object of an exemplary form of the present invention to provide an apparatus that can be used by a first individual to move the legs of a second individual without causing pain to the second individual whose legs are being moved as a result of displacing one leg relative to the other.

The foregoing objects are accomplished in an exemplary embodiment of the invention by an apparatus that wraps around and braces the ankles of the individual whose legs are to be moved, while providing a grip area between the ankles for easy movement of the legs by a caregiver.

Thus the apparatus achieves the above stated objectives, eliminates difficulties encountered in the use of prior methods, solves problems, and attains the desirable results described herein.

Further objects of an exemplary form of the present invention will be made apparent in the following Best Modes for Carrying Out Invention and the appended claims.

BRIEF DESCRIPTION OF DRAWINGS

FIG. 3 is an illustrative example of the first wrapping step.

BEST MODES FOR CARRYING OUT INVENTION

Figure 1:
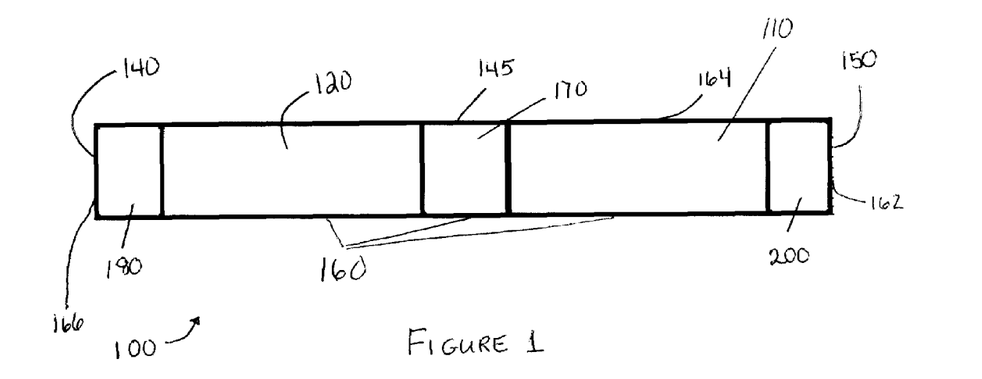
FIG. 1 is a perspective view of an exemplary mobility assistance device from above.
Figure 2:
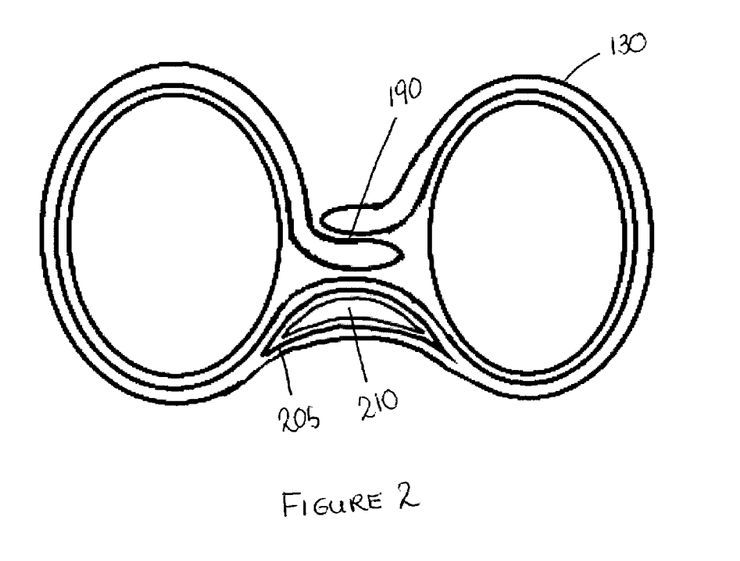
FIG. 2 is a cross sectional view of an exemplary mobility assistance device wrapped around the ankles of an individual.

Referring now to the drawings, and in particular to FIG. 1, shown therein is an exemplary embodiment of a mobility assistance device, generally identified by reference numeral 100. In the exemplary embodiment illustrated, the mobility assistance device 100 comprises a flexible strip 110. An exemplary strip 110 is rectangular, with a long narrow shape and has an inner surface 120, an outer surface 130, a first end 140, a center 145, a second end 150, and edges 160, 162, 164, 166. The outer surface 130 is identified more clearly in FIG. 2. An exemplary strip 110 also has a variable thickness, as can be seen in FIG. 2. The thickness of the center 145 as illustrated by reference numeral 2 is greater that the thickness at the first and second ends, illustrated by reference numerals 4 and 6.

Figure 8:
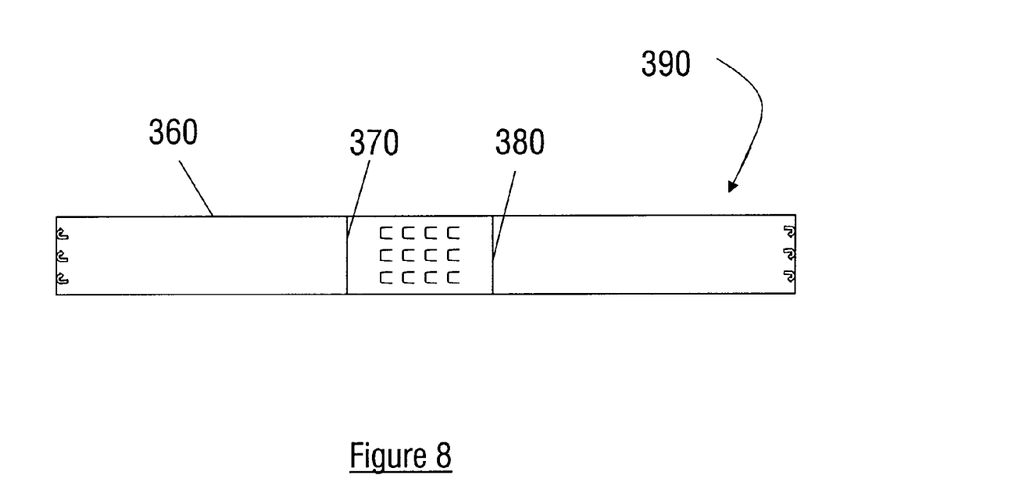
FIG. 8 illustrates a plurality of rows of fasteners.

In an exemplary embodiment, the strip 110 includes fasteners 170, 180, 190, and 200 on the center inner surface, on the inner and outer surfaces 120, 130 of the first end 140, and on the inner surface 120 of the second end 150, respectively. In the exemplary embodiment illustrated, the fasteners 170, 180, 190, and 200 are hook and loop tape, well known to those skilled in the art. In the exemplary embodiment illustrated, fasteners 170 and 190 are loop tape and fasteners 180 and 200 are hook tape. In other embodiments, different fasteners may be used. Other suitable exemplary fasteners include snaps, buttons, and hook and eye fasteners. In the event such fasteners mate precisely, such as snaps, buttons, and hook and eye fasteners, an exemplary embodiment may include parallel rows of fasteners. An example of this placement with hooks and eyes is illustrated FIG. 8. This permits a single mobility assistance device 100 to be used for a variety of size patients. Still other fasteners will be apparent to those skilled in the art.

In the exemplary embodiment discussed above, the fasteners were placed to permit the second end 150 to overlap the first end 140, with the first end 140 releasably attached to the center 145, and the second end releasably attached to the first end 140. In other exemplary embodiments other closing arrangements may be used. For example, the first end 140 could abut the second end 150 but not overlap, the first end 140 could overlap the second end 150 but not be attached to the center 145, or the second end 150 could overlap the first end 140. If hook and loop tape are used for fasteners, this exemplary embodiment would minimize the risk that the hook tape would scratch the legs of the individual whose legs are being moved. Each of these arrangements, and others that will be obvious to those skilled in the art, are within the scope of the mobility assistance device described herein. Alternate closing arrangements may require adjustment of the fastener placement from the exemplary arrangement described herein.

In an exemplary embodiment the strip 110 further includes a pocket 205 between the inner and outer surface 120, 130 having an opening 190 along the edge 160 of strip 110, as can be seen in FIG. 2. The pocket 205 is adapted to hold a small soft semi-firm insert 210, such as a folded washcloth, a multi-layered terry-cloth form, a foam or other soft molded form, or other similar object adapted to space the ankles slightly, to provide support, and to provide a grip for the caregiver.

In the exemplary embodiment illustrated, the strip 110 is made from a rectangular piece of fabric that is initially wider than the final dimensions, and comprises a plurality of layers folded lengthwise and sewn or otherwise fastened together to make the final strip 110. One suitable fabric is a polyester/cotton blend. Generally, most woven fabrics that substantially maintain their dimensions when pulled in the direction of the grain are suitable fabrics. Other suitable fabrics will be apparent to those skilled in the art. In addition to fabric, there may be other suitable material from which the strip 110 may be formed.

A mobility assistance device may be made by selecting a fabric rectangle which has a length approximately the length and approximately four times the width of the strip 110 being made. A suitable width is around fourteen inches, resulting in a strip 110 with a width of around three and one half inches. For smaller patients a suitable length is around thirty-eight inches. For larger patients a suitable length is around forty-six inches. The word "around," as in this herein, is intended to indicate that the dimensions described are flexible. A suitable width for strip 110 may vary considerably, as long three layers of the strip may be grasped easily in one hand. Similarly, a suitable length for the strip 110 may also vary considerably, as long as the strip 110 can be wrapped around the ankles of the individual whose legs are to be moved without being tight enough to cut off circulation or loose enough to permit excessive motion of one ankle with respect to the other.

Figure 9:
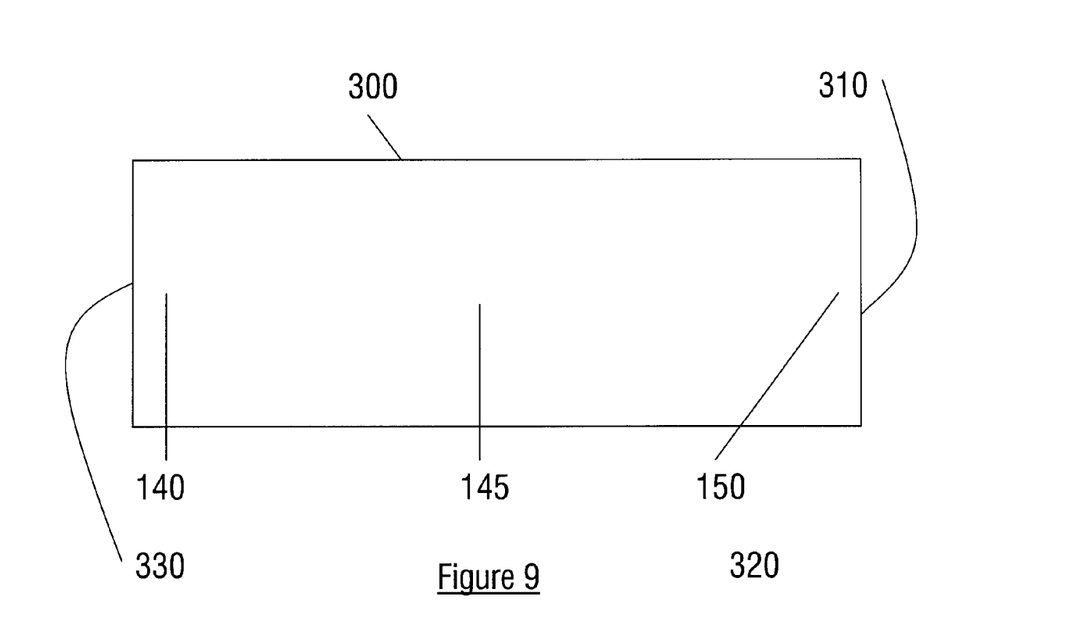
FIGS. 9-11 illustrate an exemplary process for making a mobility assistance device.

As illustrated in FIG. 9, an exemplary fabric rectangle has first through fourth edges 300, 310, 320, 330. The exemplary fabric rectangle also includes a first end 140, second end 150, and center 145 corresponding to the first end 140, second end 150, and center 145 of the strip 110 that is being made. The exemplary fabric rectangle is folded lengthwise bringing the first and third edges 300, 320 into alignment with each other and creating a first folded piece of fabric 350 having a first fold 340 and an opposing edge comprising the aligned first and third edges 300, 320. In the exemplary embodiment illustrated, the first and third edges 300, 320 of the fabric are joined together. In other exemplary embodiments, all layered edges may be joined together.

Figure 10:
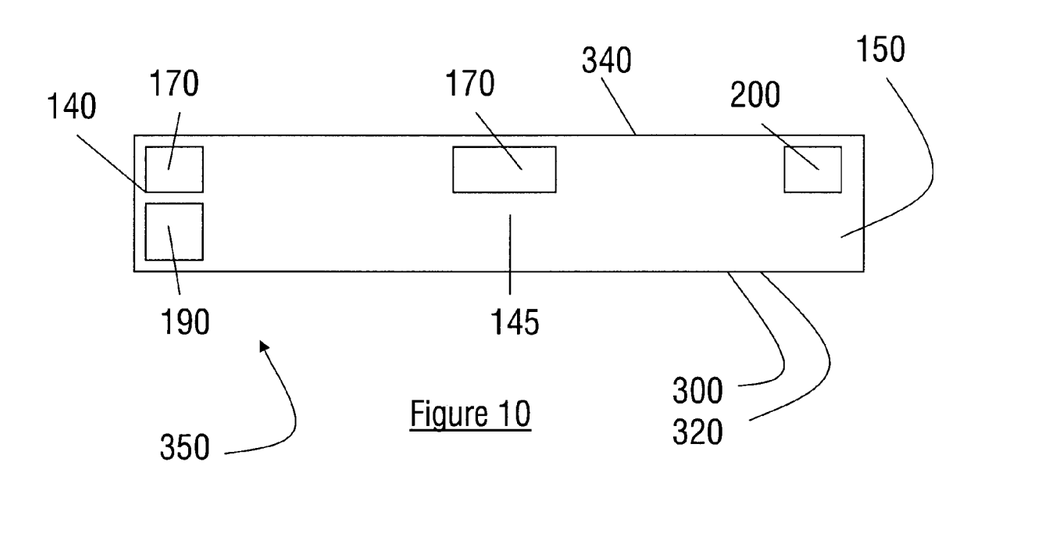

Fasteners are then affixed to the first folded piece of fabric 350. As illustrated in FIG. 10, in the first exemplary embodiment, a second fastener 190, comprising a piece of hook tape, is affixed adjacent the first end 140 and the first fold 340. A fourth fastener 200, comprising a piece of hook tape, is affixed adjacent the second end 150 and the first fold 340. A first fastener 170, comprising a piece of loop tape, is affixed adjacent the center 145 and the first fold 340. A third fastener 180, comprising a piece of loop tape, is affixed adjacent the first end 140 and the aligned first and third edges 300, 320. In another exemplary embodiment, the second and fourth fasteners 190 and 200 may be omitted in order to avoid the hook tape of second fastener 190 scratching the legs of the individual whose legs are being moved.

Figure 11:
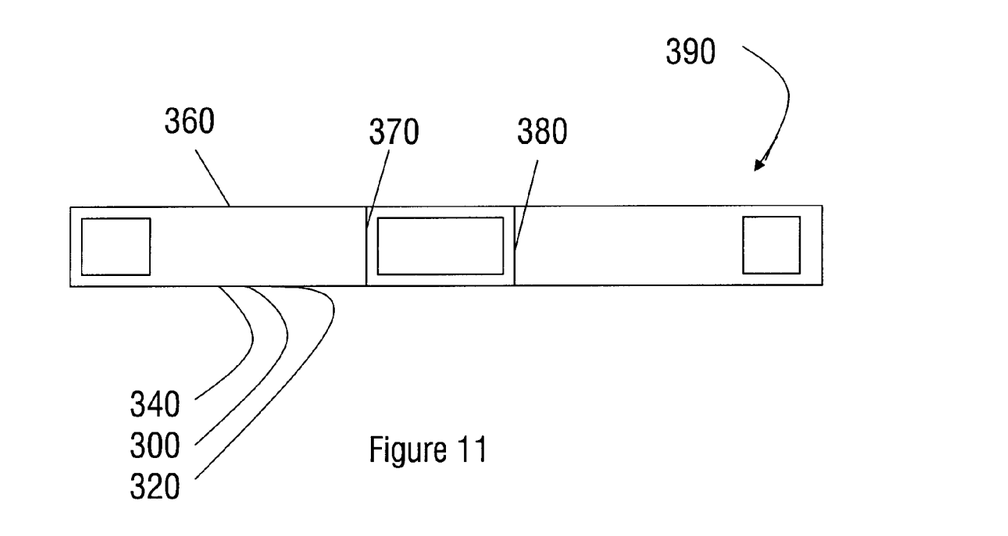

The first folded piece of fabric 350 is then folded in half lengthwise keeping the fasteners 170, 180, 190, 200 on the outside. This creates a second fold 360, bringing the first fold 340 into alignment with aligned first and third edges 300, 320, and forming a second folded piece of fabric 390, as illustrated in FIG. 11. In the exemplary embodiment illustrated, all four layers are then joined together along two spaced apart parallel lines 370, 380 extending perpendicularly from the second 360 fold to the aligned first fold 340, first and third edges 300, 320. All aligned but not joined edges are then joined with the exception of the edges between the two parallel lines 370, 380. Leaving the space between lines 370 and 380 open creates a pocket 205 between the layers of fabric. Pocket 205 is best seen in FIG. 2.

One exemplary means for joining the layers of fabric together is by sewing a seam. In other exemplary embodiments different joining methods may be used. For example, some fabric is heat sensitive, and layers of fabric may be joined by applying heat to create a seam. Other means of joining fabric, or other suitable material, that are or become known to those skilled in the art are within the subject matter described herein.

Another exemplary embodiment of a mobility assistance device 100 comprises a strip 110 made of foam covered by a fabric layer. In one exemplary embodiment of such a strip 110, the foam may be formed with a bulkier area in the center 145 that would eliminate the need for a pocket 205 and a separate insert 210. In other exemplary embodiments, the strip 110 may be made from any flexible material that is generally inelastic in a direction parallel to the longer dimension of the strip 110. If a material with sharp corners or rough surfaces is selected for use, such as leather or flexible plastic, the strip 110 may need to be padded along the sharp corners or rough surfaces in order to prevent injuring the patient during use. The material for such padding may be relatively thick fabric, or a layer of foam, or any similar material that softens the sharp edges of the strip 110 material.

Figure 4:
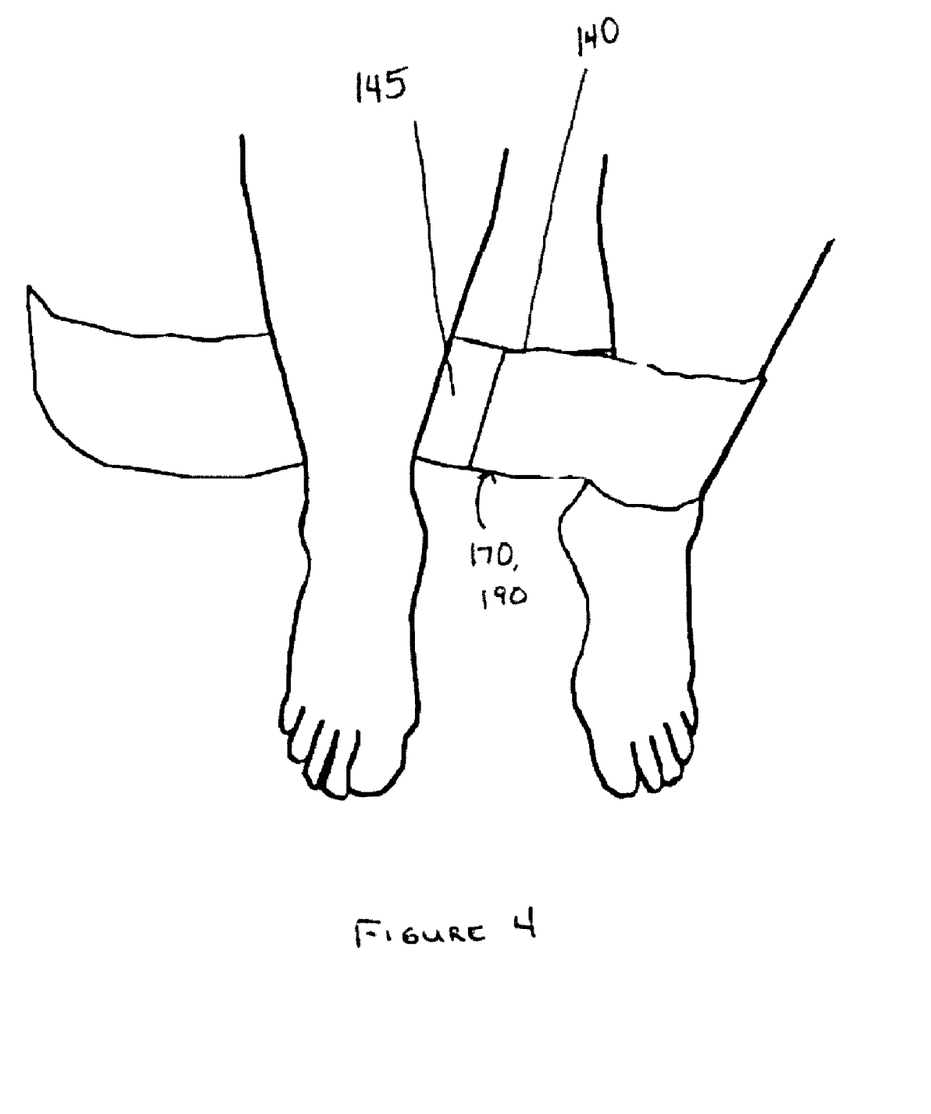
FIG. 4 is an illustrative example of the second wrapping step.
Figure 5:
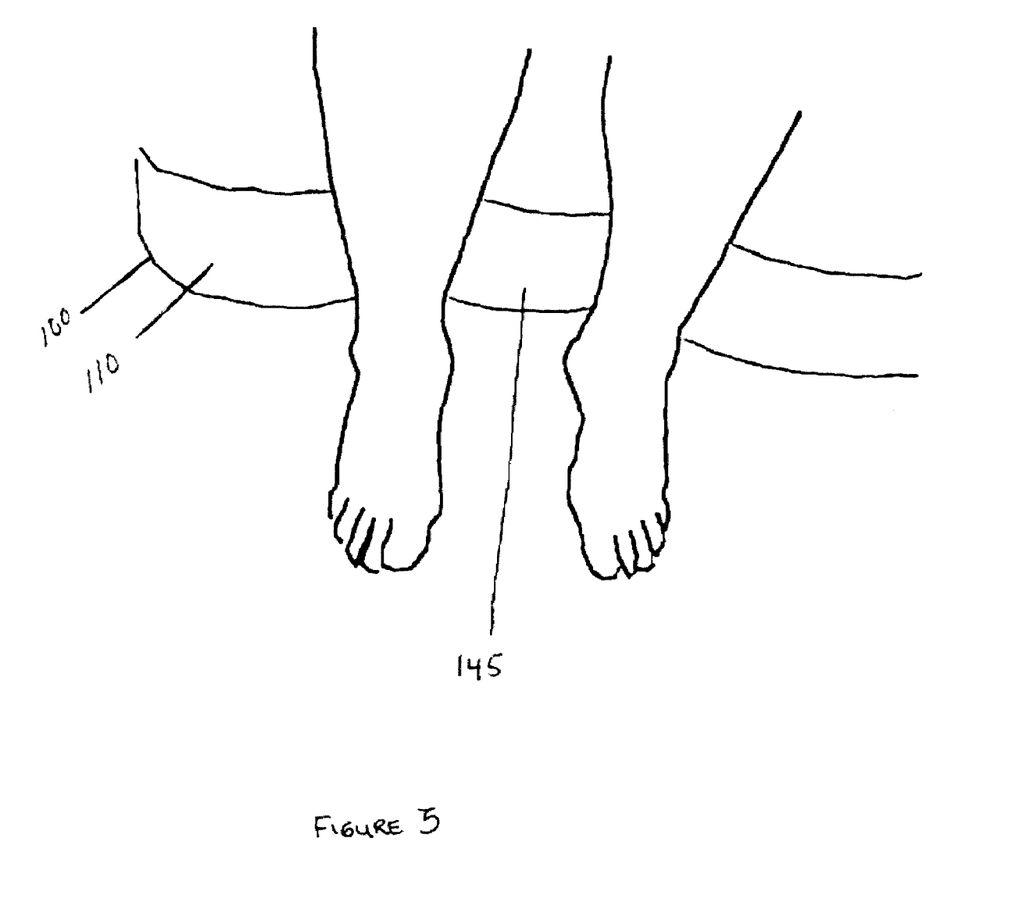
FIG. 5 is an illustrative example of the third wrapping step.

The use of an exemplary mobility assistance device 100 is illustrated in FIGS. 2 through 7. As illustrated in FIG. 3, the caregiver initially slides the mobility assistance device 100 under the ankles of the patient, positioning the center 145 of the strip 110 directly below the gap between the patient's ankles with the inner surface facing upward. In FIG. 4, the next step is illustrated. The caregiver wraps the first end 140 around the left ankle and attaches the inner surface 120 of the first end 140 to the center 145 by joining fasteners 170 and 190. Next, as illustrated in FIG. 5, the caregiver wraps the second end 150 around the right ankle, and fastens the inner surface 120 of the second end 150 to the outer surface 130 of the first end 140 by joining fasteners 180 and 200. This results in the legs being fastened loosely together as illustrated in cross section in FIG. 2.

Although in the exemplary embodiment illustrated and discussed in detail herein the inner surface 120 of the first end 140 is joined to the center 145 on the inner surface 120 of the strip 110, and the inner surface 120 of the second end 150 is joined to the outer surface 130 of the first end 150, there are many variations on the order of the particular surfaces to be joined that will be apparent to those skilled in the art. For example, in another exemplary embodiment the second end may be wrapped around the right ankle before the first end is wrapped around the left ankle. In still another exemplary embodiment both ends may be joined to the center, rather than overlapping each other. In another exemplary embodiment, the first end 140 and the center 145 may not include fasteners, and thus may not be joined to each other, in order to avoid such fasteners abrading the skin of the individual's legs. These variations, and other similar variations in order of wrapping or the extent of the overlap, if any, of the first and second ends and kind and location of the fasteners are within the scope of the mobility assistance device described herein.

Figure 6:
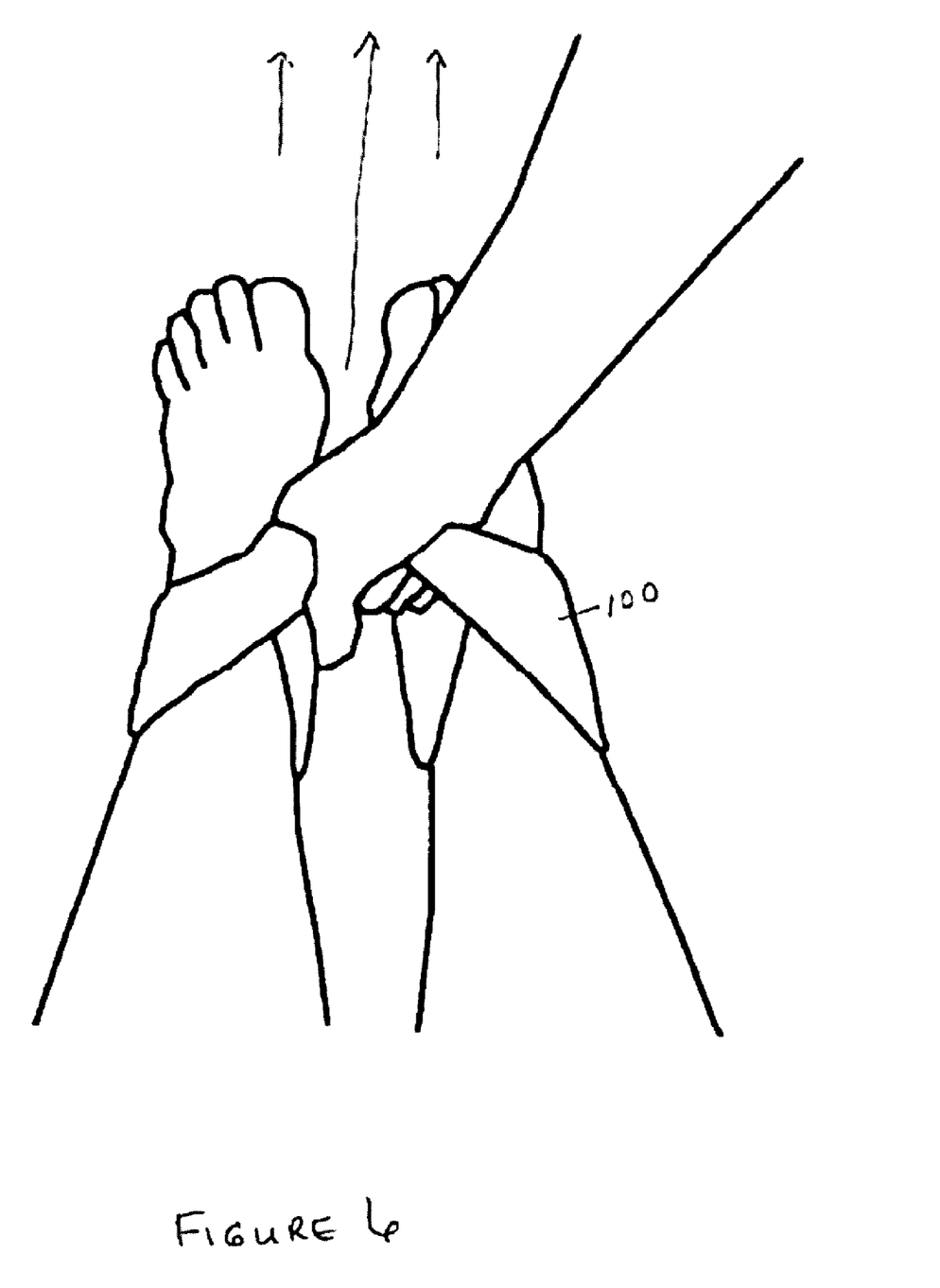
FIGS. 6-7 illustrate movement of a patient's legs using the mobility assistance device.
Figure 7:
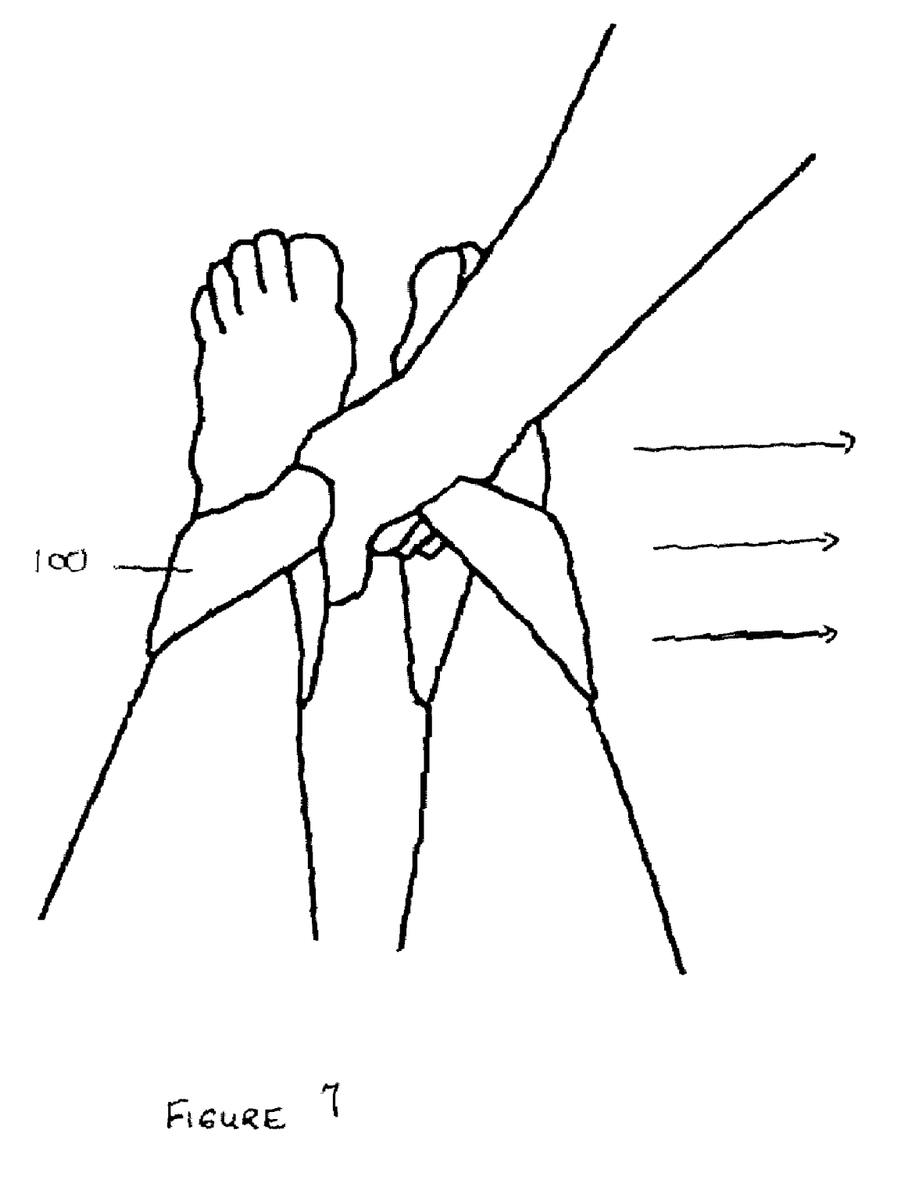

Once the mobility assistance device 100 is wrapped around the ankles, the caregiver grasps the mobility assistance device between the ankles, as illustrated in FIG. 6 and lifts the legs of the patient vertically until the legs are off the surface on which the patient is resting. Once the legs clear the surface, the caregiver uses the mobility assistance device to rotate the lower portion of the patient's body into the desired position. As illustrated in FIG. 7, this will likely involve rotating the patient's legs using the hips as a pivot point, perhaps to permit the patient to sit on the edge of a bed. Once the movement is completed, the mobility assistance device 100 may be unfastened and removed.

The insert 210 in the center of the strip 110 serves to prevent the ankles from crossing during the moving process. In addition, it provides a grip by which the caregiver can easily manipulate the patient's legs, regardless of any difference in relative sizes of the caregiver and the patient. In addition, fastening the strip around both ankles prevents the ankles from moving away from each other during the moving process, which would also be painful for the patient. It also permits the caregiver to focus on the entire patient and the process of moving the patient, rather on the specific but crucial task of ensuring that the legs maintain their position relative to each other.

The mobility assistance device 100 may also be useful for other individuals who have difficulty moving for other reasons. It is generally difficult to hold and move both legs of another individual. The mobility assistance device may be used to simplify the task by binding the ankles together and providing an easy grip to use to lift and move both legs simultaneously. Even when hip surgery is not involved, jostling two legs around and against each other may cause pain. As a specific non-limiting example, elderly individuals are often prone to tissue injury and have fragile bones. Moving the legs of an elderly individual to assist him or her in getting in and out of bed can be difficult, painful, and may cause a long term injury, such as a broken hip, if it is not done carefully. The mobility assistance device may be used to decrease the risk that providing assistance will result in pain or a more permanent injury. Other examples of instances when using a mobility assistance device would simplify the task of providing mobility assistance is with individuals who have difficulty moving because of paralysis, broken bones, or obesity.

In addition to being used directly by a caregiver, a mobility assistance device 100 may also be used to assist the patient in self mobility by adapting it to be attached to an overhead lifting apparatus. Using a series of ropes and pulleys and swivel posts, an individual may be able to lift and swing his or her own legs into the desired position. With an individual whose legs are immobile, a mobility assistance device 100 could even be left wrapped around the individual's ankles, at least for brief periods in the absence of a caregiver, permitting the individual to move about more easily using aids such as mentioned above. Such an arrangement might permit an individual with paraplegia greater independence than he or she might otherwise have.

In the foregoing description certain terms have been used for brevity, clarity, and understanding, however no unnecessary limitations are to be implied therefrom because such terms are used for descriptive purposes and are intended to be broadly construed. Moreover, the descriptions and illustrations herein are by way of examples and the invention is not limited to the exact details shown and described.

In the following claims any feature described as a means for performing a function shall be construed as encompassing any means known to those skilled in the art to be capable of performing the recited function and shall not be limited to the structures shown herein or mere equivalents thereof.

Having described the features, discoveries and the principles of the invention, the manner in which it is constructed and operated and the advantages and useful results attained; the new and useful structures, devices elements, arrangements, parts, combinations, systems, equipment, operations, methods, and relationships are set forth in the appended claims.

What is claimed is:

1. An apparatus comprising
  a mobility assistance device further comprising
    a thin, generally rectangular, flexible strip characterized by a width, a length which is adapted to permit said strip to be wrapped around two human ankles, and a thickness and which strip further has
      a first end,
      a second end,
      a center, wherein
        the thickness of the center is greater than the thickness of the first and second ends, and
        the center includes two edges which are generally parallel to the length of the strip, no more than one of which is open to accommodate an object,
      an inner surface, and
      an outer surface,
    a plurality of fasteners affixed to locations selected from the first end of the strip, the second end of the strip, and the center of the strip on the inner surface, wherein the fasteners are adapted to permit the releasable attachment of the first end to at least one of the second end and the center and to permit the releasable attachment of the second end to at least one of the first end and the center.

2. The apparatus of claim 1 wherein the fasteners comprise hook and loop tape.

3. The apparatus of claim 1 wherein the fasteners comprise hooks and eyes.

4. The apparatus of claim 1 wherein the fasteners comprise snaps.

5. The apparatus of claim 1 wherein
a first fastener is affixed to the inner surface of the strip adjacent the first end of the strip and a second fastener adapted to mate with the first fastener is affixed to the inner surface of the strip adjacent the center of the strip, and
a third fastener is affixed to the outer surface of the strip adjacent the first end of the strip and a fourth fastener adapted to mate with the third fastener is affixed to the inner surface of the strip adjacent the second end of the strip.

6. The apparatus of claim 1 wherein
a first fastener is affixed to the inner surface of the strip adjacent the first end and a second fastener adapted to mate with the first fastener is affixed to the outer surface of the strip adjacent the second end.

7. The apparatus of claim 1 wherein the strip is made of fabric.

8. The apparatus of claim 1 wherein the strip is made of a woven polyester/cotton blend fabric.

9. The apparatus of claim 1 wherein the strip is made of a plurality of layers of fabric and wherein the center of the strip comprises an insert and a pocket located in the center of the strip which is formed between two of the plurality of layers of the fabric, which pocket is adapted to hold the insert, thereby making the thickness of center of the strip greater than the thickness of the first and second ends of the strip.

10. The apparatus of claim 9 wherein the insert comprises a washcloth, folded to approximately the size of the pocket.

11. The apparatus of claim 9 wherein the insert is made of semi-firm foam.

12. A method for moving the legs of an individual comprising the steps of
placing the mobility assistance device of claim 1 beneath both ankles of an individual with the center of the strip centered between the ankles,
wrapping the first end of the strip around one of the ankles of the individual to bring the first end of the strip adjacent the center of the strip,
wrapping the second end of the strip around the other ankle of the individual to bring the second end of the strip adjacent the center of the strip,
fastening the first end of the strip to at least one of the second end of the strip and the inner surface of the center of the strip,
fastening the second end of the strip to at least one of the first end of the strip and the inner surface of the center of the strip,
grasping all layers of the mobility assistance device at the center of the strip between the ankles of the individual, and
moving the legs of the individual by
pulling upward on the mobility assistance device,
moving the mobility assistance device to the right or left, causing the legs of the individual to pivot using the hips as a pivot point, and
lowering the mobility assistance device when the legs have reached the desired rotation.

13. The method of claim 12 wherein
in the first listed fastening step the at least one of the second end of the strip and the inner surface of the center of the strip comprises the inner surface of the center of the strip, and in the second listed fastening step the at least one of the first end of the strip and the and the inner surface of the center of the strip comprises the first end of the strip.

14. The method of claim 12 wherein
in the first listed fastening step the at least one of the second end of the strip and the inner surface of the center of the strip comprises the second end of the strip, and
in the second listed fastening step the at least one of the first end of the strip and the and the inner surface of the center of the strip comprises the first end of the strip.

15. The method of claim 12 wherein the mobility assistance device is made using the following steps:
selecting a rectangular piece of fabric which has a width, length, first through fourth edges, first end, second end, and center, wherein the first and second ends and the center correspond to the first and second ends and the center of the resulting strip, and wherein the width of the fabric is approximately four times the width of the resulting strip and the length of the fabric is approximately the length of the resulting strip,
folding the rectangular piece fabric in half lengthwise to form a first folded piece of fabric comprising two layers and having opposing parallel edges comprising respectively a first fold and aligned first and third edges of the rectangular piece of fabric,
affixing at least one fastener to the first folded piece of fabric adjacent the first fold and adjacent at least one of the first end, the second end, and the center,
affixing at least one fastener to the first folded piece of fabric adjacent the overlapped first and third edges of the rectangular piece of fabric and the first end,
folding the first folded piece of fabric in half lengthwise to form a second folded piece of fabric having four layers bounded by four edges, with the first and third edges being parallel and comprising respectively a second fold and the overlapping first fold and overlapped first and third edges of the rectangular piece of fabric, and the second and fourth edges corresponding to the second and fourth edges of the strip,
joining all layers of the second folded piece of fabric together along two parallel lines near the center, which lines extend perpendicularly from the second fold to the overlapping first fold and overlapped first and third edges of the rectangular piece of fabric to create a central pocket.

16. The method of claim 15 wherein
in the first listed affixing at least one fastener step, the step comprises affixing a third fastener to the first folded piece of fabric adjacent the first fold and the second end, and in the second listed affixing at least one fastener step, the step comprises affixing a fourth fastener to the first folded piece of fabric adjacent both the overlapped first and third edges of the rectangular piece of fabric and the first end.

17. The method of claim 16 wherein the fourth fasteners comprises hook tape and the third fasteners comprises loop tape.

18. An apparatus comprising
a mobility assistance device further comprising
a thin generally rectangular flexible strip comprising a plurality of layers of fabric and characterized by width, length, and thickness, and which strip has an inner surface and an outer surface and which strip further has
a first end,
a second end, and
a center, wherein the center includes a center pocket formed between two of the plurality of layers of fabric, which center pocket is open on no more than one edge parallel to the length of the strip, an insert adapted to be inserted in the center pocket thereby creating a thickness in the center of the strip that is greater than the thickness of the first and second ends, a plurality of fasteners affixed to the strip comprising a piece of loop tape affixed adjacent the first end on the outside surface of the strip, and a mating piece of hook tape affixed adjacent the second end on the inner surface of the strip.

19. The apparatus of claim 18 wherein the insert comprises a multi-layered terry-cloth form.

20. The apparatus of claim 18 wherein the fabric comprises a woven polyester/cotton blend.

21. The apparatus of claim 18 wherein the plurality of layers of fabric are formed by folding a single larger piece of fabric in quarters lengthwise.

22. The apparatus of claim 18 wherein the length of the strip is around thirty-eight inches and the width of the strip is around four and one fourth inches.

23. The apparatus of claim 18 wherein the length of the strip is around forty-six inches and the width of the strip is around four and one fourth inches.

* * * * *